(12) United States Patent
Graupe

(10) Patent No.: US 8,280,516 B2
(45) Date of Patent: Oct. 2, 2012

(54) METHOD AND APPARATUS FOR CLOSED-LOOP DEEP BRAIN STIMULATION IN TREATING NEUROLOGICAL DISEASES

(76) Inventor: Daniel Graupe, Highland Park, IL (US)

( * ) Notice: Subject to any disclaimer, the term of this patent is extended or adjusted under 35 U.S.C. 154(b) by 328 days.

(21) Appl. No.: 12/459,213

(22) Filed: Jun. 29, 2009

(65) Prior Publication Data

US 2010/0094377 A1 Apr. 15, 2010

Related U.S. Application Data

(60) Provisional application No. 61/195,527, filed on Oct. 9, 2008.

(51) Int. Cl.
*A61N 1/00* (2006.01)
(52) U.S. Cl. .................................................. 607/48
(58) Field of Classification Search ............... 607/2, 45, 607/46, 48, 96; 340/539.12; 600/300, 26
See application file for complete search history.

(56) References Cited

U.S. PATENT DOCUMENTS

| | | | |
|---|---|---|---|
| 6,016,449 A | 1/2000 | Fischell | |
| 6,094,598 A | 7/2000 | Elsberry et al. | |
| 6,227,203 B1 | 5/2001 | Rise et al. | |
| 6,463,328 B1 * | 10/2002 | John | 607/45 |
| 7,006,872 B2 | 2/2006 | Gielen | |
| 7,463,927 B1 | 12/2008 | Chaouat | |
| 2002/0116042 A1 | 8/2002 | Boling | |
| 2002/0161403 A1 | 10/2002 | Meadows et al. | |
| 2003/0195602 A1 | 10/2003 | Boling | |
| 2005/0187589 A1 | 8/2005 | Wallace | |
| 2005/0240086 A1 * | 10/2005 | Akay | 600/300 |
| 2006/0058854 A1 | 3/2006 | Abrams et al. | |
| 2006/0217781 A1 * | 9/2006 | John | 607/45 |

(Continued)

FOREIGN PATENT DOCUMENTS

WO WO-2004/034880 4/2004

(Continued)

OTHER PUBLICATIONS

"International Search Report and Written Opinion", by Officer David Pereda Cubian in PCT Application No. PCT/US09/043637, Jun. 8, 2009, 3 pages.

(Continued)

*Primary Examiner* — George Manuel
*Assistant Examiner* — Robert Wieland
(74) *Attorney, Agent, or Firm* — Todd S. Hofmeister; Michael Best & Friedrich LLP

(57) ABSTRACT

A system that incorporates teachings of the present disclosure may include, for example, a device having a stimulation sequence generator device, at least one implantable electrode for insertion in a brain of a human being, where the at least one implantable electrode is coupled to the stimulation sequence generator, a sensor for placement on a body part of the human being, and a controller coupled to the stimulation sequence generator device and the sensor. The controller can be operable to receive a signal from the sensor, extract from the signal characteristics corresponding to desirable movements of the body part of the human being to generate output data, detect a condition from the output data for predicting an upcoming tremor, and cause the stimulation sequence generator device to apply a stimulation to the at least one implantable electrode for a first period responsive to the detected condition to prevent the upcoming tremor.

18 Claims, 4 Drawing Sheets

U.S. PATENT DOCUMENTS

| | | | |
|---|---|---|---|
| 2007/0025608 A1 | 2/2007 | Armstrong | |
| 2007/0208212 A1* | 9/2007 | DiLorenzo | 600/26 |
| 2007/0239054 A1 | 10/2007 | Giftakis et al. | |
| 2008/0033508 A1 | 2/2008 | Frei | |
| 2008/0046012 A1 | 2/2008 | Covalin et al. | |
| 2008/0058773 A1* | 3/2008 | John | 604/891.1 |
| 2009/0082691 A1 | 3/2009 | Denison et al. | |
| 2010/0094377 A1 | 4/2010 | Graupe | |
| 2010/0217341 A1* | 8/2010 | John et al. | 607/2 |
| 2011/0251583 A1 | 10/2011 | Miyazawa et al. | |

FOREIGN PATENT DOCUMENTS

| | | |
|---|---|---|
| WO | WO-2006/110206 | 10/2006 |
| WO | WO-2007/058788 | 5/2007 |
| WO | WO-2008/027233 | 3/2008 |

OTHER PUBLICATIONS

"Written Opinion of the International Searching Authority", Patent Cooperation Treaty, by Officer David Pereda Cubian, in PCT Application No. PCT/US2009/043637, Nov. 17, 2010, 8 pages.

Graupe, "Principles of Artificial Neural Networks", University of Illinois, Chicago, USA; World Scientific, Advanced Series on Circuits and Systems—vol. 6 2nd Edition (Cover), 1 page.

Graupe, "Time Series Analysis, Identification and Adaptive Filtering", Robert Krieger Publishing Company, Malabar, Florida; 2nd Edition (Cover), 1 page.

Graupe, Daniel et al., "Adaptively controlling deep brain stimulation in essential tremor patient via surface electromyography", Neurological Research, vol. 32, No. 9, 2010, 899.

\* cited by examiner

100

200

300

400

METHOD AND APPARATUS FOR CLOSED-LOOP DEEP BRAIN STIMULATION IN TREATING NEUROLOGICAL DISEASES

PRIOR APPLICATION

The present application claims the benefit of priority to U.S. Provisional Application No. 61/195,527 filed on Oct. 9, 2008.

FIELD OF THE DISCLOSURE

The present disclosure relates generally to neurological disorders, and more specifically to a method and an apparatus for managing a neurological disorder by deep brain stimulation in closed loop continuously responsive to measurements from the patient in real time.

BACKGROUND

Neurological disorders such as Parkinson's disease can be a chronic, progressive neurodegenerative movement disorder whose primary symptoms include tremors, rigidity, slow movement, poor balance and difficulty walking and in speech. When a person has Parkinson's disease, his/her dopamine-producing cells in the brain begin to die. Dopamine is responsible for sending information to the parts of the brain that control movement and coordination. Hence, as the amount of dopamine produced decreases, messages from the brain directing the body how and when to move are delivered in a slower fashion, leaving a person incapable of initiating and controlling movements in a normal way.

Deep Brain Stimulation (DBS) is a surgical therapy for movement disorders that represents an advancement in the treatment of Parkinson over the last 50 years. DBS uses a surgically implanted, battery-operated thin neuron-stimulator to reverse in large part the abnormal function of the brain tissue in the region of the stimulating electrode.

Commercially available DBS systems typically include a neuron-stimulator, an extension, and a lead. The neuron-stimulator is placed under skin operating as a battery powered electrical impulse generator implanted in the abdomen. The extension is a wire also placed under the skin (from the head, down the neck, to the abdomen) to bring the signals generated by neuron-stimulator to the lead. The lead is an insulated coiled wire with four electrodes implanted deeply in the brain to release the electrical impulse. Presently DBS devices operate only in open loop, namely, they are not continuously responsive to patient's status at a given instance of time but are fixed once the DBS electrodes are surgically implanted.
Innovative Aspects of the Present Invention Achieving closed-loop control of DBS where control is continuously responsive to measurements at any given time, using noninvasive surface EMG sensors which sense integrated motor-neuron activity in the vicinity of the electrode through the skin (say, at muscles and limbs including facial muscles, fingers, and vocal cord) and/or implanted sensors.

In preferred realizations of this invention, processing of the data obtained from said sensors and the resulting control decision and control command signals are also performed in a noninvasive manner, these control commands being transmitted by wireless to the implanted device.

In some realization of this invention, measurements of patient's status are solely obtained from sensors that are non-invasive.

In preferred realizations of the present invention, signal processing involves prediction of time of next tremor and detecting and subsequent filtering out of desirable movements.

In realizations as in, sensing and control are then applicable to most existing DBS systems and do not require redesign of presently implanted DBS systems except for installing a miniature wireless receiver.

In some realizations, the stimulating electrode serves also as a sensing electrode, as is accomplished via electronic switching of connection and of impedance, to eliminate need for a separately implanted sensing electrode in the stimulated site of the patient's brain.

DETAILED DESCRIPTION

Figure 1:
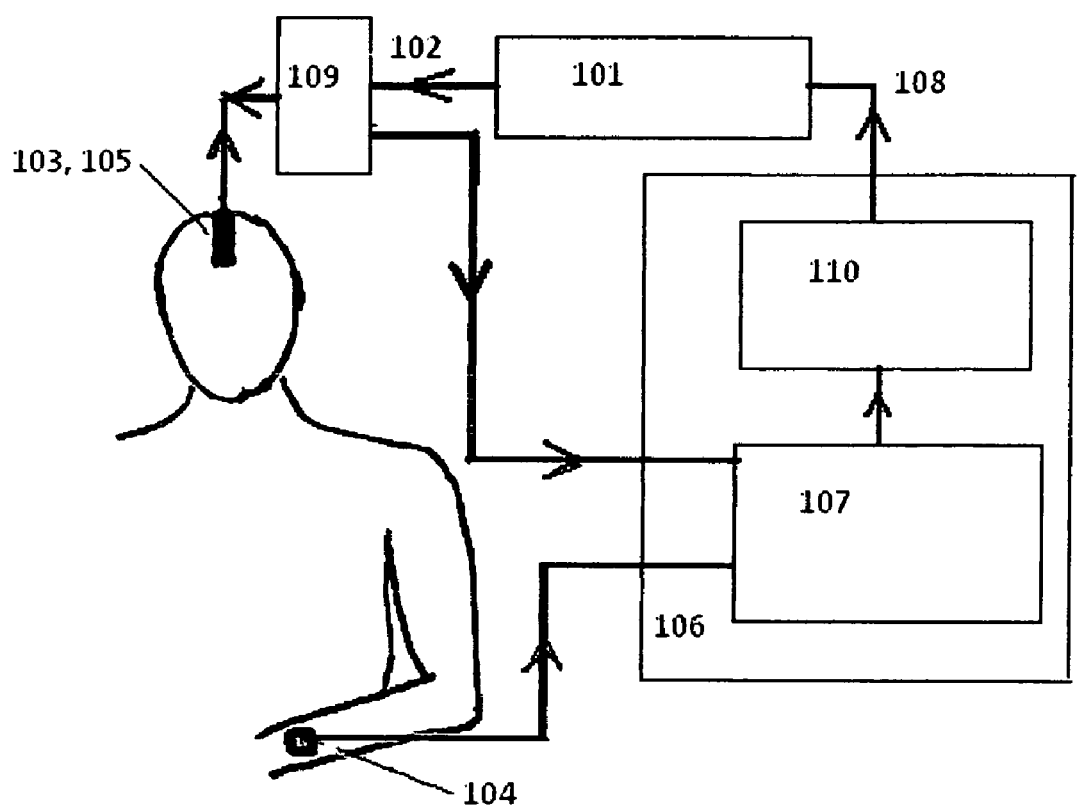
FIG. 1 is a schematic of the Closed Loop Deep-Brain Stimulator

An embodiment of the present disclosure entails:

A stimulation signal sequence generating system and device (SSG) 101 which generates an train of impulses (TI) 102 that are applied to implanted deep-brain stimulation electrodes (IDSTE) 103 for the purpose of DBS. See FIG. 1.

Clinical testing of Parkinson Disease (PD) patients has shown that after a period T of several seconds, over which stimulation is applied and where tremors and other PD symptoms are suppressed, when stimulation is stopped, there is an interval V over which abnormal symptoms return, where V is also of the order of a few seconds, often approaching T above. Reaching that point can be detected by either sensory electrodes (ISE) implanted in the vicinity of where stimulation is being applied (in the CNS), or by minute changes in parameters derived from surface EMG signals sensed by surface (non-invasive) EMG (electro-myographic) skin-electrodes (EMGE) 104 on certain muscles, say, on the patient's wrist. The start-times and end-times of intervals T and V can be detected via the processing of data from surface-EMG sensors and/or implanted deep brain sensors (IDSE) 105 as discussed below. See FIG. 1.

The invention incorporates a DBS system with a feedback controller device (FCD) 106 to detect the reaching of the critical levels for starting and stopping of stimulation as above, which consists of an implanted deep brain sensory electrode (IDSE) 105 implanted in the vicinity of where DBS is being applied and/or noninvasive surface EMG skin electrodes (EMGE) 104 attached to certain of the patient's muscles (at certain limbs, or other muscles). See FIG. 1.

The above IDSE 105 and EMGE 104 electrodes send their sensory signals to a signal processing device (SP) 107, where the signal parameters are extracted (say as in Ch 5 of: D. Graupe, Time Series Analysis, Identification and Adaptive Filtering, $2^{nd}$ edition, Krieger Publ. Co., 1989, or by using wavelet transforms as in RM Rao and AS Bopardikar, Wavelet Transforms, Addison Wesley, 1998) which allow prediction of eventual return of symptoms such as tremors before they actually occur and the detection and filtering of normal and desirable movements of the patient to discriminate signal parameters due to these from undesirable symptoms such as tremors, say incorporating artificial neural network algorithms as in D. Graupe, Principles of Artificial Neural Networks, $2^{nd}$ Edition, World Scientific, 2007, and where a threshold-decision and prediction algorithm determines that another train of stimulation signals is to be applied. See FIG. 1.

The SP device 107 is part of the controller device (FCD) 106 where, on the basis of the prediction and movement discrimination performed in the SP 107, an on-off control command (CC) 108 is sent from the control-and-decision device CDD 110 of the FCD 106 to a DBS sequence generator (SSG) 101, to start and stop DBS stimulation. See FIG. 1.

The SSG 101 generates a DBS stimulation sequence and sends it to the implanted DBS stimulation electrodes (IDSTE) 103 in accordance with the CC 108 above. See FIG. 1.

The IDSE 105 and the IDSTE 103 are physically the same electrode, while performing two functions, namely, sensing (IDSE) 105 and stimulation (IDSTE) 103, as determined by an electronic switch (ESW) 109 which may be an optical switch, noting that stimulation pulses (the pulse-width) last only approximately 50 to 100 microseconds while the interval between these pulses is of the order of 5 to 7 milliseconds, namely 5000 to 7000 microseconds (i.e., stimulation pulse rate is approximately 150 to 200 pulses per second). Hence, the "idle time" between two successive stimuli last approximately 99% of the inter-pulse interval and is available for sensing. The ESW 109 may be housed in the SSG 101. See FIG. 1.

The ESW 109 switches the implanted stimulation electrode (IDTSE) 103 between sending a stimulation pulse from the SSG 101, namely serving as IDSTE 103 and serving as sensor of the voltage at the vicinity of where stimulation is being applied, namely, serving as IDSE 105, thus sending its information to the SP 107 that is located in the FCD 106. See FIG. 1. It does so at usually predetermined fixed intervals, based on the actual pulse width and pulse rate of any given DBS system.

Figure 2:
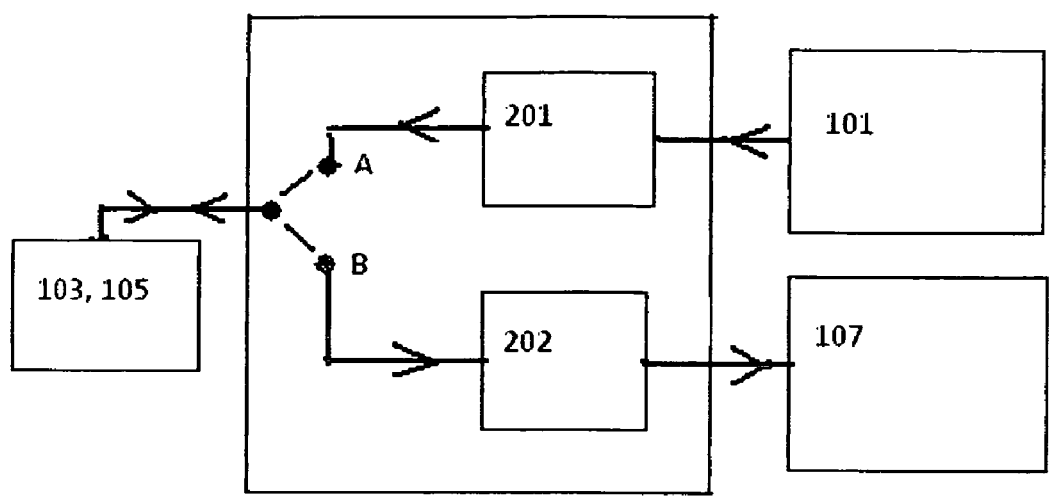
FIG. 2 describes the functions of the electronic switch (ESW)

ESW 109 also serves to switch impedances between the one needed for stimulation 201and the impedance needed for sensing 202. See FIG. 2.

Figure 3:
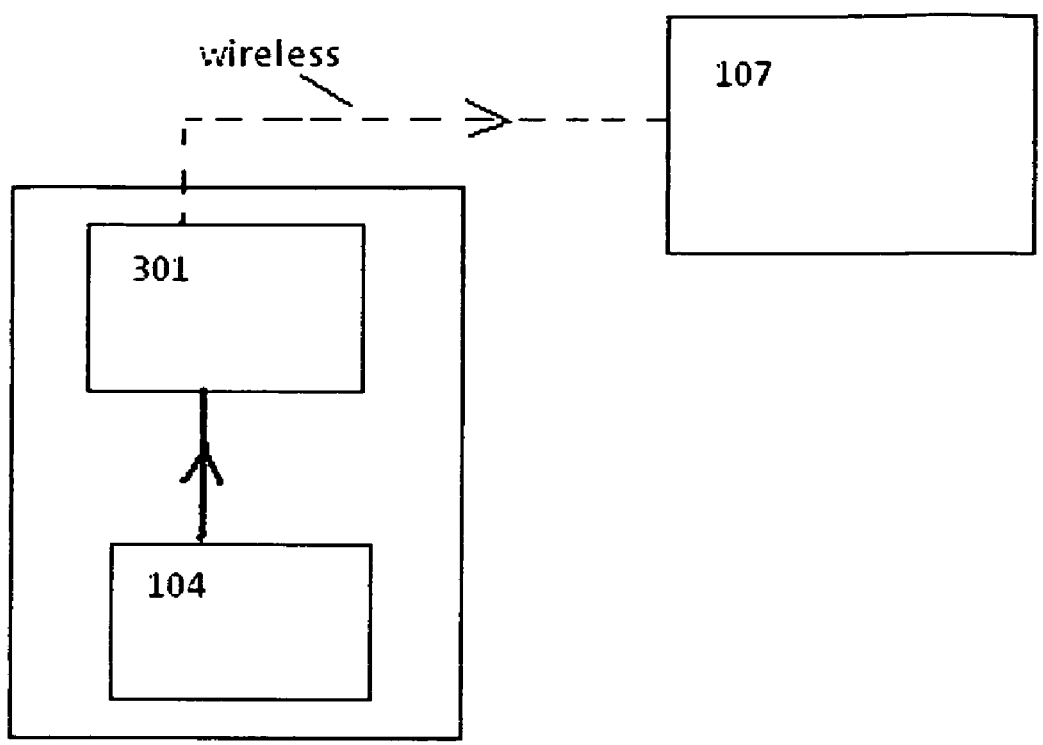
FIG. 3 describes the EMG electrodes (EMGE) assembly with the wireless transmitter chip (WTM)

The EMGE electrodes 104 may incorporate a wireless transmitter microchip (WTM) 301 to transmit the sensed information to a signal processing and control subsystem that is incorporated in the FCD 106. See FIG. 3.

The above would result in facilitating the application of DBS only when needed, rather then applying DBS continuously (until the physician stops it in a clinical session), as is the present practice. This will avoid overstimulation and protecting the patient from possible side effects due to unnecessarily prolonged stimulation in terms of applying a dose of electrical charge to the stimulated site that is higher than needed.

By our invention, effective stimulation time may be reduced (by our simulation results) by a factor of 2 or better. Furthermore, battery drainage will be reduced by the same factor. We comment that T and modulation levels are determined to maximize the mean ratio of V/T, noting that T and V change as determined by the controller.

Figure 4:
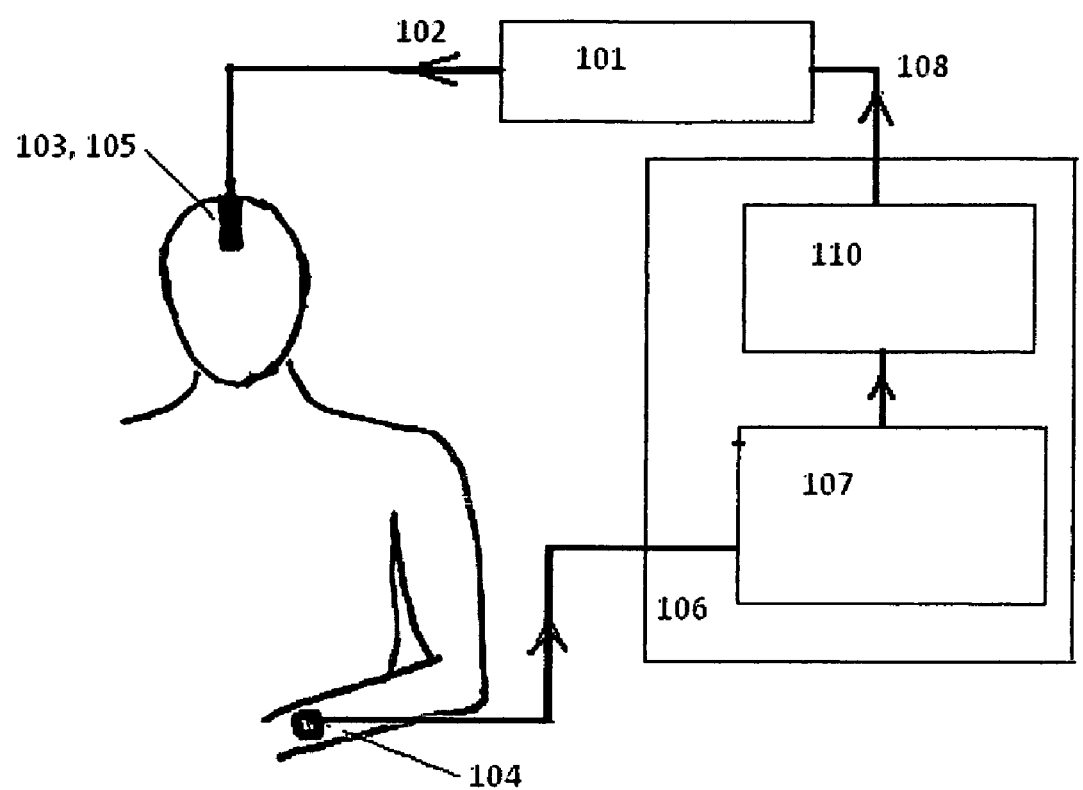
FIG. 4 is a schematic of the Closed-Loop Stimulator using only EMGE sensors

By our invention, when no implanted sensors are employed, namely, when sensing is only via EMG electrodes, then closed-loop DBS requires only noninvasive sensing (See FIG. 4). It can then operate with conventional open-loop DBS system, to which only noninvasive sensing electrodes are added as is a noninvasive addition of an SP 107 device or algorithm to an existing on-off controller that is usually noninvasive too. If however, invasive (implanted) sensors (IDSE) 105 are incorporated, still, no additional sensing electrode need to be implanted, since switching and impedance matching allow using the stimulation electrode 103 to also serve as sensor.

What is claimed is:

1. A device, comprising:
   a stimulation sequence generator device;
   at least one implantable electrode for insertion in a brain of a human being, wherein the at least one implantable electrode is coupled to the stimulation sequence generator;
   a surface-electromyographic (EMG) sensor for placement on a body part of the human being; and
   a controller coupled to the stimulation sequence generator device and the sensor, wherein the controller is operable to:
   receive a signal from the surface-EMG sensor;
   extract from the signal characteristics corresponding to desirable movements of the body part of the human being to generate output data;
   detect a condition from the output data for predicting an upcoming tremor; and
   cause the stimulation sequence generator device to apply a stimulation to the at least one implantable electrode for a first period responsive to the detected condition to prevent the upcoming tremor.

2. The device of claim 1, wherein the controller is operable to calculate surface-EMG parameters from the signal.

3. The device of claim 2, wherein the surface-EMG parameters are dynamic time series parameters of a stochastic surface-EMG.

4. The device of claim 3, wherein the stochastic surface-EMG comprises one of autoregressive model parameters, autoregressive and moving average parameters, wavelet model parameters, or equivalents or derivatives thereof, and wherein the controller is operable to predict the condition of the upcoming tremor from the surface-EMG parameters.

5. The device of claim 1, wherein the controller is operable to detect the condition by compensating for a time difference between a neural firing and a tremor detected from signals supplied by the surface-EMG sensor.

6. The device of claim 3, wherein a compensation performed by the controller is predictive such that the controller is operable to cause the stimulation sequence generator device to restart the stimulation before tremors have been predicted to occur.

7. The device of claim 1, wherein the surface-EMG sensor comprises at least one implantable sensing electrode, and wherein the controller is operable to detect the condition from a predetermined threshold level in parameters extracted from the signal, which indicate abnormal effects of a neurological disorder which would re-appear unless stimulation is restarted, and wherein the pre-determined threshold level is adjustable.

8. The device of claim 1, wherein the surface-EMG sensor is a surface raw-EMG electrode, wherein the controller is operable to detect the condition from a pre-determined threshold-level in parameters extracted from the signal, which indicate abnormal effects of a neurological disorder which would re-appear unless stimulation is restarted, and wherein the predetermine threshold level is adjustable.

9. The device of claim 1, wherein no implanted sensors are employed by the device.

10. The device of claim 1, wherein the surface-EMG sensor includes an acceleration sensor.

11. The device of claim 1, wherein the surface-EMG sensor is a noninvasive sensor, and wherein the noninvasive sensor wirelessly transmits signals to the controller.

12. The device of claim 1, comprising an electronic switching device coupled to the stimulation sequence generator device in order that the at least one implantable electrode can be switched from operating as at least one sensor electrode to at least one stimulation electrode, wherein the controller is operable to:
cause the electronic switching device to enter a first state for applying the stimulation to the at least one implantable electrode; and
cause the electronic switching device to enter a second state to allow the at least one implantable electrode to serve as another sensor in addition to the surface-EMG sensor.

13. The device of claim 12, wherein the electronic switching device serves to cause a first impedance change of the at least one implantable electrode when the at least one implantable electrode serves as the at least one stimulation electrode, and wherein the electronic switching device serves to cause a second impedance change of the at least one implantable electrode when serving as the at least one sensor electrode.

14. The device of claim 12, where the controller is operable to integrate information from at least one of the surface-EMG sensor or the at least one implantable electrode when operating as the at least one sensor electrode utilizing a neural network.

15. The device of claim 1, where the controller is operable to discriminate between a desired motor function and a tremor or other abnormal motor function from the signal supplied by the surface-EMG sensor.

16. The device of claim 15, wherein the controller is operable to use a neural network to perform the discrimination.

17. The device of claim 12, wherein the electronic switching device is an optical switch.

18. The device of claim 12, wherein the controller is operable to:
cause the at least implantable electrode to serve as the at least one stimulation electrode for the first period; and
cause the at least implantable electrode to serve as the at least one sensing electrode after the first period for a subsequent period.

* * * * *